United States Patent
O'Young et al.

(10) Patent No.: US 7,163,582 B2
(45) Date of Patent: Jan. 16, 2007

(54) SYSTEM AND METHOD OF PRODUCING BISPHENOL-A (BPA) USING DIRECT CRYSTALLIZATION OF BPA IN A SINGLE CRYSTALLIZATION STAGE

(75) Inventors: Drow Lionel O'Young, West Covina, CA (US); Shan Tao Hsieh, Princeton Junction, NJ (US); Vaibhav Kelkar, West Covina, CA (US)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/661,169

(22) Filed: Sep. 12, 2003

(65) Prior Publication Data

US 2004/0204616 A1    Oct. 14, 2004

Related U.S. Application Data

(63) Continuation-in-part of application No. 10/099,227, filed on Mar. 13, 2002.

(51) Int. Cl.
  *C30B 7/05*    (2006.01)
(52) U.S. Cl. ............... 117/68; 117/69; 422/245.1; 422/250
(58) Field of Classification Search ............. 422/245.1, 422/250; 117/68, 69
See application file for complete search history.

(56) References Cited

U.S. PATENT DOCUMENTS

| | | | |
|---|---|---|---|
| 1,978,949 A | 10/1934 | Kohn et al. | |
| 2,191,831 A | 2/1940 | Perkins et al. | |
| 2,730,553 A | 1/1956 | Williamson et al. | |
| 2,775,620 A | 12/1956 | Williamson et al. | |
| 2,791,616 A | 5/1957 | Luten, Jr. et al. | |
| 3,164,640 A | 1/1965 | Bostian et al. | |
| 3,326,986 A | 6/1967 | Dugan et al. | |
| 3,972,950 A | 8/1976 | Kwantes | |
| 4,053,522 A | 10/1977 | McClure et al. | |
| 4,079,087 A | 3/1978 | Sun | |
| 4,107,218 A * | 8/1978 | Konrad et al. | 568/724 |
| 4,141,924 A | 2/1979 | Sun | |
| 4,191,843 A | 3/1980 | Kwantes et al. | |
| 4,209,646 A | 6/1980 | Gac et al. | |
| 4,294,994 A | 10/1981 | Li | |
| 4,308,404 A | 12/1981 | Kwantes et al. | |
| 4,308,405 A | 12/1981 | Kwantes | |
| 4,354,046 A | 10/1982 | Ladwig et al. | |
| 4,354,048 A * | 10/1982 | Strom | 568/730 |
| 4,369,293 A | 1/1983 | Heydenreich et al. | |
| 4,391,997 A | 7/1983 | Mendiratta | |
| 4,400,555 A | 8/1983 | Mendiratta | |
| 4,443,635 A | 4/1984 | McLaughlin | |
| 4,492,807 A | 1/1985 | Aneja | |
| 4,514,574 A | 4/1985 | Inoue et al. | |
| 4,529,823 A | 7/1985 | Mendiratta | |

(Continued)

*Primary Examiner*—Robert Kunemund
(74) *Attorney, Agent, or Firm*—Dorsey & Whitney LLP

(57) ABSTRACT

A system and method are provided for producing Bisphenol-A (BPA) using direct crystallization of BPA in a single crystallization stage. In one embodiment the method comprises reacting Phenol and Acetone in the presence of a catalyst to form a product solution including Bisphenol-A and Phenol; removing a part of the Phenol from the product solution if required, and providing a selective amount of solvent, so as to obtain a product solution with the desired phase equilibrium behavior; and feeding the product solution with a selective composition to a crystallization stage operated at a selected temperature, so as to recover substantially pure Bisphenol-A in crystal form.

11 Claims, 9 Drawing Sheets

U.S. PATENT DOCUMENTS

| | | | |
|---|---|---|---|
| 4,533,764 A | 8/1985 | Chang et al. | |
| 4,590,303 A | 5/1986 | Mendiratta | |
| 4,638,102 A | 1/1987 | Little | |
| 4,740,635 A | 4/1988 | Gomes de Matos et al. | |
| 4,820,740 A | 4/1989 | Li | |
| 4,847,433 A | 7/1989 | Kissinger | |
| 4,859,803 A | 8/1989 | Shaw | |
| 4,861,919 A | 8/1989 | Robbins et al. | |
| 4,906,789 A | 3/1990 | Grzywa et al. | |
| 4,927,973 A | 5/1990 | Dong et al. | |
| 4,927,978 A | 5/1990 | Buechele et al. | |
| 5,008,470 A | 4/1991 | Powell et al. | |
| 5,015,784 A | 5/1991 | Rudolph et al. | |
| 5,059,721 A | 10/1991 | Powell et al. | |
| 5,075,511 A | 12/1991 | Li | |
| 5,105,026 A | 4/1992 | Powell et al. | |
| 5,198,591 A | 3/1993 | Kiedik et al. | |
| 5,210,329 A | 5/1993 | Gomes de Matos et al. | |
| 5,269,887 A | 12/1993 | Jakob et al. | |
| 5,288,926 A | 2/1994 | Patrascu et al. | |
| 5,300,700 A | 4/1994 | Malamet et al. | |
| 5,302,774 A | 4/1994 | Berg et al. | |
| 5,315,042 A | 5/1994 | Cipullo et al. | |
| 5,324,867 A | 6/1994 | Asaoka et al. | |
| 5,345,000 A | 9/1994 | Moriya et al. | |
| 5,368,827 A * | 11/1994 | Moriya et al. | 422/245.1 |
| 5,371,304 A | 12/1994 | Asaoka et al. | |
| 5,382,712 A | 1/1995 | Asaoka et al. | |
| 5,395,857 A | 3/1995 | Berg et al. | |
| 5,399,784 A | 3/1995 | Asaoka et al. | |
| 5,414,151 A | 5/1995 | Pressman et al. | |
| 5,434,316 A | 7/1995 | Kissinger | |
| 5,475,152 A | 12/1995 | Kissinger et al. | |
| 5,502,016 A | 3/1996 | Kiedik et al. | |
| 5,512,700 A | 4/1996 | Patrascu et al. | |
| 5,545,764 A | 8/1996 | Berg et al. | |
| 5,629,457 A | 5/1997 | Zhang et al. | |
| 5,648,561 A * | 7/1997 | Tan et al. | 568/727 |
| 5,696,295 A | 12/1997 | Wulff et al. | |
| 5,698,600 A | 12/1997 | Wulff et al. | |
| 5,723,688 A | 3/1998 | Patrascu et al. | |
| 5,756,860 A | 5/1998 | Meurer et al. | |
| 5,777,180 A | 7/1998 | June et al. | |
| 5,780,690 A | 7/1998 | Berg et al. | |
| 5,783,733 A | 7/1998 | Kissinger | |
| 5,785,823 A | 7/1998 | Meurer et al. | |
| 5,786,522 A | 7/1998 | Cipullo | |
| 5,914,431 A | 6/1999 | Fennhoff | |
| 5,919,990 A | 7/1999 | Likibi | |
| 6,191,316 B1 | 2/2001 | Fennhoff et al. | |
| 6,635,788 B1 * | 10/2003 | Oyevaar et al. | 568/728 |
| 2003/0181768 A1 | 9/2003 | O'Young et al. | |

* cited by examiner

SYSTEM AND METHOD OF PRODUCING BISPHENOL-A (BPA) USING DIRECT CRYSTALLIZATION OF BPA IN A SINGLE CRYSTALLIZATION STAGE

RELATED APPLICATIONS

This patent application is a continuation-in-part application of pending U.S. patent application Ser. No. 10/099,227 filed on Mar. 13, 2002, the entire disclosure of which is expressly incorporated herein by reference, and is related to U.S. patent application Ser. No. 10/632,664 filed Aug. 1, 2003, the entire disclosure of which is expressly incorporated by reference herein.

FIELD OF THE INVENTION

The present invention provides a system and method for production of Bisphenol-A (BPA). More specifically, the present invention provides a system and method for producing Bisphenol-A wherein the phase equilibrium behavior of certain process streams is manipulated to directly recover substantially pure Bisphenol-A by crystallization from solution, without the need for the intermediate step of recovering the solid adduct of Phenol and Bisphenol-A.

BACKGROUND OF THE INVENTION

The production of bisphenols such as 2,2-bis (4-hydroxyphenyl)propane (Bisphenol-A, hereinafter sometimes referred to as "4,4-BPA" or simply identified as "BPA") is an important process as Bisphenol-A is used as a feedstock or intermediate for the production of various polymers such as epoxy resins and polycarbonates. In one application, Bisphenol-A is reacted with phosgene to produce commercial polycarbonate resins. High quality polycarbonates, such as those used as optical media in the electronics and disk drive industry, require highly pure Bisphenol-A as a feedstock. Consequently, much effort has been focused on developing processes to produce Bisphenol-A of high purity.

In general, Bisphenol-A is produced by a well known liquid-phase condensation reaction of Phenol with Acetone in the presence of an acid catalyst such as Hydrochloric acid, or more commonly, an acidic ion exchange resin as catalyst. The reaction product typically includes the desired Bisphenol-A, unreacted reactants, by-products of the reaction most notably Water, and a variety of impurities including isomers, analogs and homologs of Bisphenol-A. These include 2-(2-hydroxyphenyl)-2-(4-hydroxyphenyl)propane (hereafter referred to as the o,p-bisphenol isomer or "2,4-BPA"), dianins compound, chromans, trisphenols, polyphenols and unfavorably colored substances. A variety of processes are used to purify and recover Bisphenol-A crystals from the reaction product. Purification and recovery of the Bisphenol-A typically represents about one half or more of the total capital investment of the system, and known techniques are often very costly and energy intensive.

After the condensation reaction, the resulting mixture is often concentrated, usually by distillation, to remove unreacted Acetone, the Water of reaction, and some Phenol, prior to recovery of the Bisphenol-A product by crystallization. U.S. Pat. No. 5,783,733 describes one prior art method of producing Bisphenol-A wherein Phenol and a ketone are reacted in the presence of an ion exchange resin catalyst to produce a reaction product stream including Bisphenol-A. Prior to crystallization, excess Phenol, Water and Acetone are removed from the product stream. Crystallization, in this case melt crystallization, is used to purify the crude bisphenol. Specifically multiple stage fractional melt crystallization with successive steps of crystallization, partial melting (sweating) and total melting is used. Such Phenol removal and melt crystallization techniques are very costly in terms of capital equipment and energy consumption.

In another well known technique, an adduct of Bisphenol-A and Phenol is first obtained by crystallization, and the adduct is then broken by known methods such as extraction, distillation, dephenolation, steam stripping or prilling, yielding high purity bisphenol A.

This prior art method is described for example in U.S. Statutory Invention Registration US H1943 where the reaction product stream is fed directly to a crystallizer to form a slurry consisting of a liquid phase, and a solid crystal phase of an equal-molar adduct of Bisphenol-A and Phenol. The adduct crystals are separated from the liquid (referred to as mother liquor) and Phenol is removed from the adduct in a series of Phenol removal or dephenolation steps. Finally, multiple stage fractional melt crystallization is preformed to produce the product Bisphenol-A.

The steps to remove Phenol from the adduct are quite costly and add to the complexity of the system. Often, such steps subject the adduct of Bisphenol-A and Phenol to high temperatures of up to about 250° C., where degradation or undesirable reactions can occur.

U.S. Pat. No. 4,294,994 describes a method for removal of Phenol from the adduct of Bisphenol-A and Phenol by subjecting the adduct feed at a temperature in the range of about 50° C. to about 150° C., and under spray drying conditions typically at temperatures in the range of about 150° C. to about 250° C. with a small amount of liquid carrier having a boiling point below that of Phenol and recovering the Bisphenol-A product from the released Phenol. The purity of the obtained Bisphenol-A product is up to about 99% by weight; however, this method suffers from a significant disadvantage since the adduct of Bisphenol-A and Phenol experience high temperatures where degradation usually occurs.

Another technique to remove Phenol from the adduct is by distillation as described for example in U.S. Pat. No. 4,798,654. Specifically, the '654 patent describes a process for preparing Bisphenol-A comprising distilling the intermediate adduct of Bisphenol-A and Phenol at a temperature in a range from about 160° C. to about 200° C. in a dephenolization column; recovering Phenol from the top of the distillation column and Bisphenol-A from the bottom of the distillation column; and recycling a part of the bottom liquid to the adduct feed of Bisphenol-A and Phenol. It is said that plugging of the distillation column is prevented and continuous operation for a long period of time such as one year is possible. However, the Phenol content of the Bisphenol-A product taken out of the bottom of the dephenolization column is still up to about 2%.

While advances have been made in the production of Bisphenol-A, further improvements are needed. The aforementioned prior art methods require intermediate steps of separation of the adduct of Bisphenol-A and Phenol, and also costly steps to completely remove Phenol from the adduct, and further costly steps to obtain Bisphenol-A in pure solid form. Further, as the purity requirements for Bisphenol-A crystals become more rigorous, the complexity and costs of producing Bisphenol-A increase. Accordingly, it is desirable to provide an improved process for producing Bisphenol-A of high purity.

SUMMARY OF THE INVENTION

Accordingly, the present invention provides an improved system and method of producing Bisphenol-A.

The system and method of the present invention is described wherein the phase equilibrium behavior of a system comprised of Phenol, Bisphenol-A and a solvent is selectively controlled such that Bisphenol-A is directly crystallized from the product solution. Among the advantages, this method provides for the direct crystallization of Bisphenol-A following the reaction, without the need for the intermediate step of recovering the solid adduct of Phenol and Bisphenol-A. This leads to a considerable reduction in the number of processing steps, thereby reducing capital and energy costs, and provides for a much simpler process for the production of BPA.

Bisphenol-A is produced from a reaction of Phenol and Acetone, forming a product solution including Phenol, Bisphenol-A, isomers of Bisphenol-A, unreacted reactants such as Acetone, and by-products, most notable of which is Water. A solvent is provided in the product solution. The amount of Phenol and the Solvent in the product solution is selectively controlled to adjust the composition of the product solution which is fed to a crystallization stage, and to establish a desirable phase equilibrium behavior in the crystallizer, so as to recover substantially pure Bisphenol-A (BPA) in a single crystallization step.

The solvent is a pseudo component and may be comprised of a single component or may be comprised of a mixture of two or more solvents such that it exhibits the desired phase behavior. The boiling temperature of each solvent is selected such that the mixture will provide desirable operating conditions in terms of solubility and temperature in the crystallizer unit. It should be understood by those of ordinary skill in the art that the system may include other components or solutes; however, for purposes of the present invention the system is concerned only with the three primary components—Phenol, Bisphenol-A and a solvent—and thus the phase equilibrium of the system is characterized as a ternary system.

More specifically, in one embodiment the present invention provides a method of producing Bisphenol-A, comprising the steps of: reacting Phenol and Acetone in the presence of a catalyst to form a product solution including Bisphenol-A and Phenol; removing a part of the Phenol from the product solution if required, and providing a selective amount of solvent, so as to obtain a product solution with the desired phase equilibrium behavior; and feeding the product solution with a selective composition to a crystallization stage operated at a selected temperature, so as to recover substantially pure Bisphenol-A in crystal form. If necessary, Bisphenol-A crystals of a higher quality can be obtained via recrystallization of the solid Bisphenol-A. In this instance the crystallizer stage would contain more than one crystallizer unit providing for the recystallization steps.

In one embodiment of the invention, the solvent is composed of a mixture of Acetone and Water. This is particularly advantageous because unreacted Acetone as well as Water, a by-product of the reaction, are present in the reactor outlet stream.

In another aspect of the present invention, a system for producing Bisphenol-A is provided comprising a reactor unit wherein a product stream is produced, including at least Bisphenol-A and Phenol. A BPA crystallization stage is provided, and the composition of the stream fed to the crystallizer stage is selectively adjusted using various means, such that substantially pure Bisphenol-A is produced upon crystallization.

Of significant advantage, and contrary to the teachings of the prior art, the system and method of the present invention provides for the direct crystallization of Bisphenol-A from the product solution following the reaction, without the need for the intermediate step of recovering the adduct of Phenol and Bisphenol-A. This leads to a considerable reduction in the number of processing steps required to obtain pure BPA, thereby reducing capital and energy costs.

Of further advantage, since the intermediate adduct crystallization step is omitted, this invention eliminates the need for complete removal of Phenol from the adduct, usually carried out in expensive steps such as a dephenolation unit. Depending on the amount of excess Phenol used in the reactor over and above the stoichiometric requirement of two moles of Phenol for every mole of Acetone fed to the reactor, the process of the present invention may require only a partial removal of Phenol from the product solution, thus reducing the energy cost of Phenol vaporization considerably Furthermore, this partial Phenol removal is carried out at a much higher concentration of Phenol, and is hence much more cost effective than that in the prior art processes.

Furthermore, the present invention provides a process for recovering high quality Bisphenol-A in the crystal form directly from solution, which eliminates the need for expensive solids formation units such as a prilling tower.

Further details regarding the various aspects of this invention are provided in the remainder of the disclosure.

BRIEF DESCRIPTION OF THE DRAWINGS

Other objects and advantages of the present invention become apparent upon reading of the detailed description of the invention provided below and upon reference to the drawings in which.

DETAILED DESCRIPTION OF THE INVENTION

Background of Phase Diagrams and Projections

The inventors have discovered a system and method of producing Bisphenol-A wherein the phase equilibrium behavior of the product stream fed to a crystallizer stage (sometimes also referred to as the feed solution to the crystallizer stage) is selectively controlled to provide selected results for process operation. The invention provides for manipulation and selective control of the phase equilibrium of Bisphenol-A, Phenol and a solvent. It should be understood by those of ordinary skill in the art that the system may include other components or solutes such as impurities, unreacted reactants, isomers and the like; however, for purposes of the present invention we are concerned only with the primary components in the solution—Phenol, Bisphenol-A and solvent—where the solvent is a pseudo-component representing either a pure solvent component, or a mixture of two or more solvent components. Thus, the system is characterized as a ternary phase equilibrium system.

Figure 1:
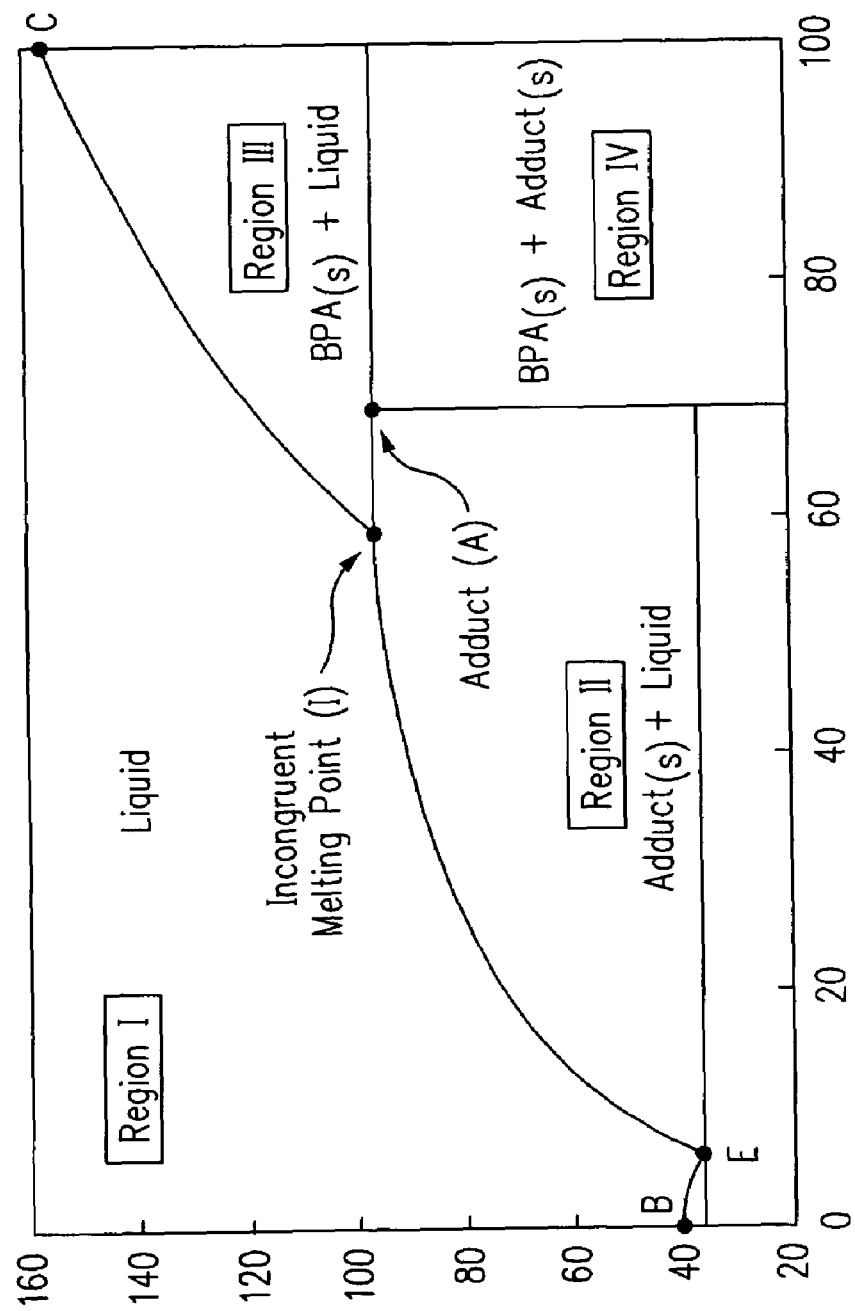
FIG. 1 is a polythermal phase equilibrium diagram for a binary system of Bisphenol-A and Phenol.

In the prior art, the phase equilibrium of the bisphenol system for crystallization is typically considered as a binary system comprised of Bisphenol-A and Phenol as shown in FIG. 1. Since pressure has little effect on the equilibria between solids and liquids, the phase changes for a binary system can be represented on a temperature-concentration diagram. A plurality of phase regions are shown. In Region I, bounded by the liquidus transition line BEIC, both components (i.e. Bisphenol-A and Phenol) are in the liquid phase. A eutectic between Phenol and the adduct of Phenol and Bisphenol-A exists at point E. An incongruent melting eutectic between Bisphenol-A and the adduct exists at point I. The incongruent melting point (I) is the point where the adduct melts, and the liquid composition and the solid composition are not the same. When the adduct of Phenol and Bisphenol-A melts, the liquid composition is at point I while some solid Bisphenol-A is formed as well. This is why the location of the adduct (point A) is between point I and pure Bisphenol-A. In Region II the solid adduct exists in equilibrium with liquid. The solid adduct is comprised of an equal-molar composition of Bisphenol-A and Phenol. In Region III solid Bisphenol-A exists in equilibrium with liquid. In Region IV both solid adduct and solid Bisphenol-A phases exist. Such a phase diagram which illustrates the relation between the temperature and composition is referred to as a polythermal phase diagram.

The approach of the prior art for the separation of Phenol from Bisphenol-A is to describe a system with only two components and this can be described by use of the binary phase diagram as illustrated in FIG. 1. However for systems with more than two components as taught by the present invention, the polythermal phase diagram is a FIGURE in multi-dimensional space. For example, the isobaric phase diagram of the ternary system of Phenol, Bisphenol-A and solvent represents an image in 3-dimensional space. The composition coordinates can be plotted in weight fractions on a triangular grid in the X-Y plane, and the temperature can be plotted on an additional vertical axis (Z axis). This leads to the polythermal phase diagram in the shape of a 3-dimensional (3D) triangular prism. However, it is not convenient to work with multi-dimensional phase diagrams. Fortunately, for this three component system, much of the important information, particularly the crystallization boundaries, can be represented on a 2-dimensional (2D) projection onto a triangular base. This is obtained by projecting the phase diagram along the temperature axis (Z axis), onto the base of the prism (X-Y plane), and is referred to as the projection of a polythermal phase equilibrium diagram.

It is a common practice at the conceptual design stage to reduce a 3D diagram to a 2D diagram as described above, for ease of visualization and for process design purposes. The projection of the polythermal diagram can be employed as a useful tool for process feasibility study because it provides the region for product recovery.

Figures 2A, 2B:
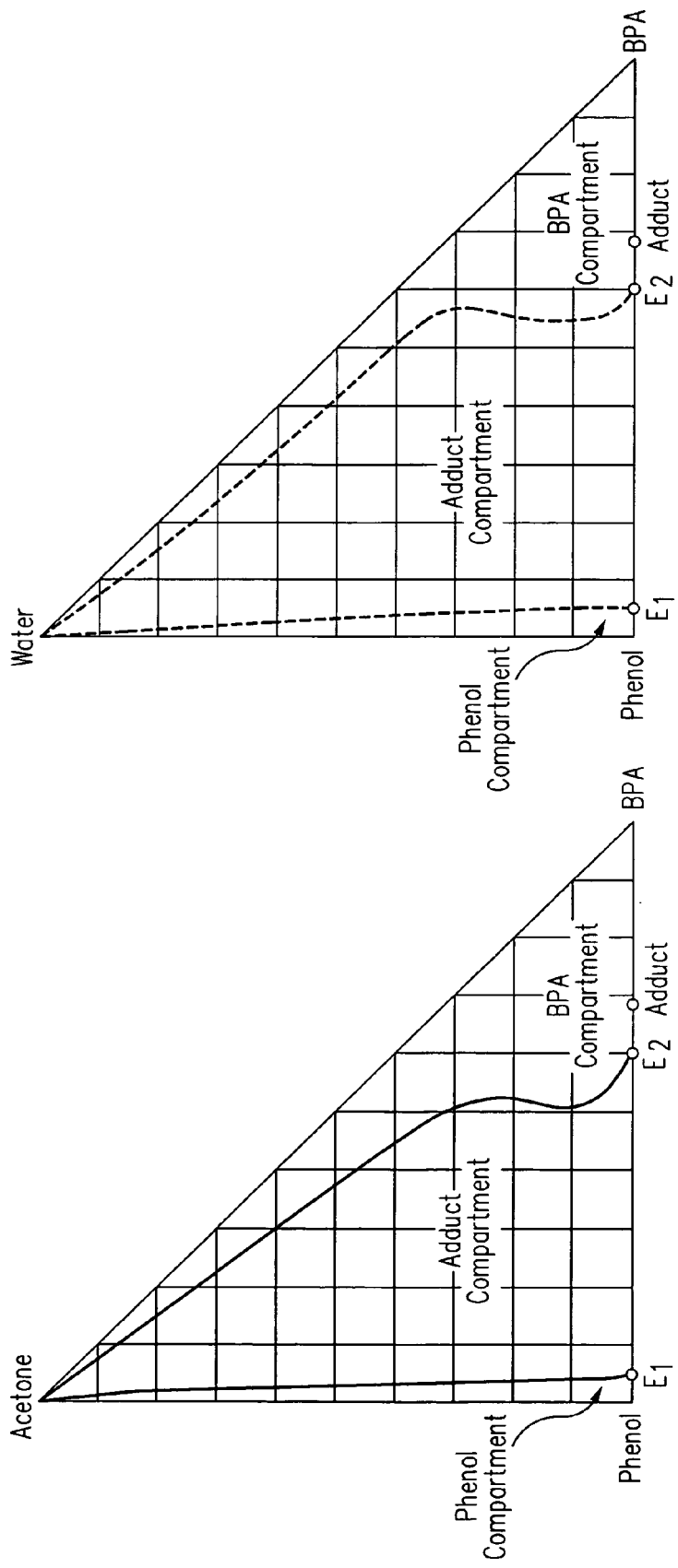
FIG. 2(a) is the polythermal projection of the phase equilibrium diagram for the ternary system of Bisphenol-A, Phenol and Acetone.
FIG. 2(b) is the polythermal projection of the phase equilibrium diagram for the ternary system of Bisphenol-A, Phenol and Water.

FIG. 2(a) illustrates the projection of the polythermal phase diagram of a ternary system comprising of Phenol, Bisphenol-A, and a solvent which in this case is Acetone. Please note that the ternary phase equilibrium diagram is represented herein as a right-angled triangle for clarity, as opposed to the alternative equilateral triangular diagram form. There are two important regions or compartments in the phase diagram for production of Bisphenol-A. One is the Bisphenol-A compartment and the other is the adduct compartment. These are identified in the illustration in FIG. 2(a). The Phenol compartment occupies only a small portion of the phase diagram, and is not important from the consideration of recovering solid Bisphenol-A. Also, a compartment where Acetone can be recovered as a solid exists near the solvent vertex. However, for low-boiling solvents such as Acetone this compartment is so small and so far away from the desired region of operation, that it can be ignored and hence has not been shown in FIG. 2(a).

When the feed composition to the crystallizer is located inside the Bisphenol-A compartment, substantially pure solid Bisphenol-A can be recovered by various means, such as cooling the mixture to an appropriate temperature, or by evaporating the solvent. When the feed composition to the crystallizer is located in the adduct compartment, solid adduct can be recovered. Thus, the projection of the polythermal phase diagram clearly delineates the regions in the composition space where a feed stream or feed solution to a crystallizer can yield solid adduct or solid Bisphenol-A. FIG. 2(b) shows the projection of a polythermal diagram for a ternary system comprising of Phenol, Bisphenol-A, and another Solvent, in this case Water. Note that as before, four phase regions are established in this phase diagram—a Bisphenol-A compartment, an adduct compartment, a Phenol compartment, and a Solvent (Water) compartment (not shown). However, the shape and location of the phase boundaries for Acetone and Water solvents are somewhat different. This is because the phase behavior of the system results from the mutual interaction of all the components present in the system, and different solvents produce a different effect on the phase behavior of the overall system.

The actual experimental data for the Phenol-BPA-Solvent system for different solvent components may be determined by those of ordinary skill in the art without undue experimentation, and is discussed in further detail in a separate section below.

Figure 3:
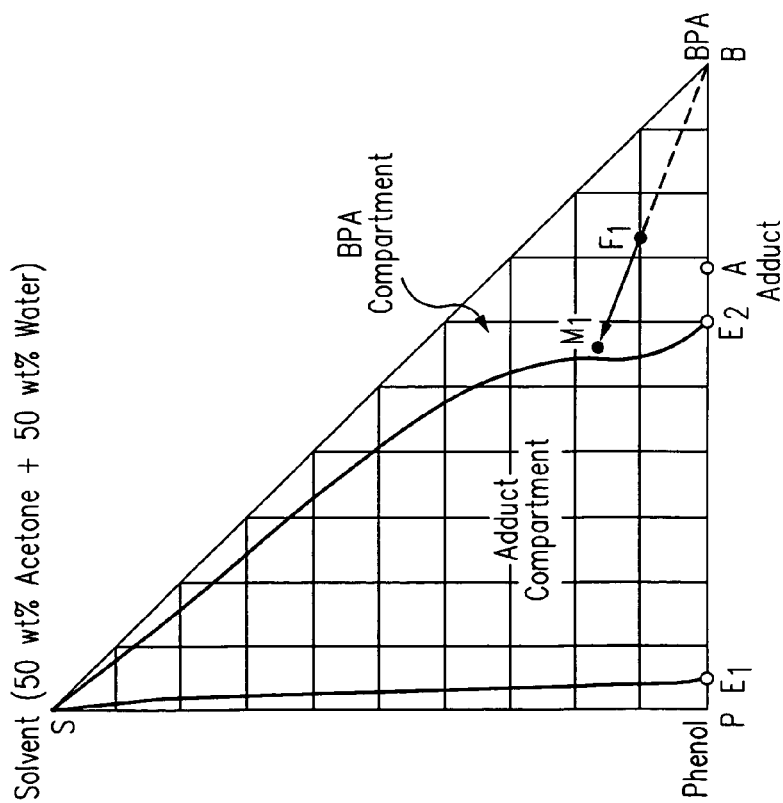
FIG. 3 is the polythermal projection of the phase equilibrium diagram for the ternary system of Bisphenol-A, Phenol and Solvent where the Solvent comprises 50% Acetone and 50% Water by weight.

In addition to identifying the regions of product recovery, the projection of the polythermal phase diagram can also be used to identify the maximum recovery of the solid from the crystallizer. Referring to FIG. 3 the projection of a polythermal phase diagram is illustrated for a ternary system of Bisphenol-A, Phenol, and a Solvent which is comprised of a mixture of 50% Acetone and 50% Water on a weight basis. Consider a feed solution to the crystallizer located at point $F_1$ in the BPA compartment, as shown in FIG. 3. During crystallization, crystals of solid Bisphenol-A are recovered from the crystallizer, while the composition of the mother liquor is given by a point on the line indicated by the arrow $F_1M_1$. The recovery of Bisphenol-A can be defined as the ratio of the mass of pure Bisphenol-A solid recovered to the mass of the feed. In FIG. 3, the maximum recovery of Bisphenol-A is given by the ratio of $F_1M_1$ to $BM_1$, because both Bisphenol-A and adduct solid would co-exist once the composition of the mother liquor reaches the phase boundary $SE_2$.

Feasible movement for the system within the composition space can be provided by varying or changing of one or more of the following three parameters: temperature (typically cooling), adding of an "anti solvent," meaning a component that has the opposite effect of the solvent, or evaporation of the solvent.

When considering the process design, it is important to control the composition, and hence the location on the phase diagram, of two points, namely the feed to the crystallizer, and the outlet from the crystallizer (the outlet from the crystallizer is commonly referred to as the mother liquor). In order to only crystallize the desired product, both these two points must lie within the desired product's compartment in the phase diagram. These two points will be collinear with a third point, which is the composition of the solid being crystallized. Also, to maximize the per pass recovery of the desired solid product from the crystallizer, the two points representing the compositions of the crystallizer feed and the crystallizer outlet (the mother liquor) should have a large separation in their location. Thus, referring to the present system, a good process for producing Bisphenol-A will try to control the crystallizer feed and the crystallizer outlet composition within the Bisphenol-A compartment, while having a maximum distance between the two.

Method of the Present Invention

The present invention is now described in more detail. In contrast to the prior art, the inventors have discovered a system and method of producing Bisphenol-A wherein the phase equilibrium behavior of a feed solution to a crystallizer—a ternary system comprising Bisphenol-A, Phenol and a Solvent—is selectively controlled, in order to recover substantially pure Bisphenol-A crystals in a crystallization step.

This is a very powerful tool and allows one to manipulate the process operation by varying process operating conditions such as, but not limited to, the type of solvent(s); concentration ratio of solvent components employed; mass concentration of any one of, or combination of, Phenol, Bisphenol-A and the solvent fed to the crystallizer; the amount of catalyst in the reactor; the feed rate of any one of, or combination of, the reactants fed to the condensation reactor; or recycled feed rates of any of the relevant constituents.

More specifically, in one embodiment of this invention, a method of producing Bisphenol-A is provided wherein a product solution is first produced by a condensation reaction of Phenol and Acetone, and is comprised of at least Phenol and Bisphenol-A, and additionally isomers of Bisphenol-A and un-reacted reactants. A solvent is provided in the product solution. The solvent may be added to the product solution after the reaction. Alternatively, at least a portion of the solvent may already be present in the product solution following the reaction. The product solution is fed to a crystallization stage, and the composition of this stream, as well as the crystallizer operation conditions are selectively controlled in order to establish the desired phase behavior, such that substantially pure Bisphenol-A is crystallized from the solution.

The composition of the product solution at the feed to the crystallizer may be adjusted in a variety of ways. Any one of, or combination of, Phenol, Bisphenol-A in solution, the solvent, or mixture of solvent components may be added to, or removed from, the product solution prior to the crystallizer to adjust the feed composition such that it lies in the desired crystallization compartment. Alternatively, the composition of reactants fed to the reactor and the reaction conditions such as Temperature, Pressure, the amount of catalyst and the flow velocity of reactants in the reactor, the percentage conversion of Acetone, and the like may be adjusted to provide the desired composition in the product solution from the reactor. For example, the ratio of Phenol to Acetone in the reactor feed may be varied to provide a certain weight or mol percent of Phenol in the product solution.

The solvent may be comprised of one component, or alternatively may be comprised of a mixture of two or more solvents components. Suitable solvents include but are not limited to: Water; ketones such as Acetone, MEK and MIBK; alcohols such as Methanol, Ethanol, IPA, 2-BuOH, t-BuOH, and 1,2-EG; amines such as DMA, NMP; hydrocarbons such as aromatic hydrocarbons; and other solvents such as DMF and DMSO.

Since Acetone is a reactant and is present in the system, it is useful to employ as a solvent. Also, since Water is a by-product of the reaction, it is a logical choice for a solvent. In a preferred embodiment of the invention, the solvent is comprised of a mixture of Acetone and Water.

Figure 4:
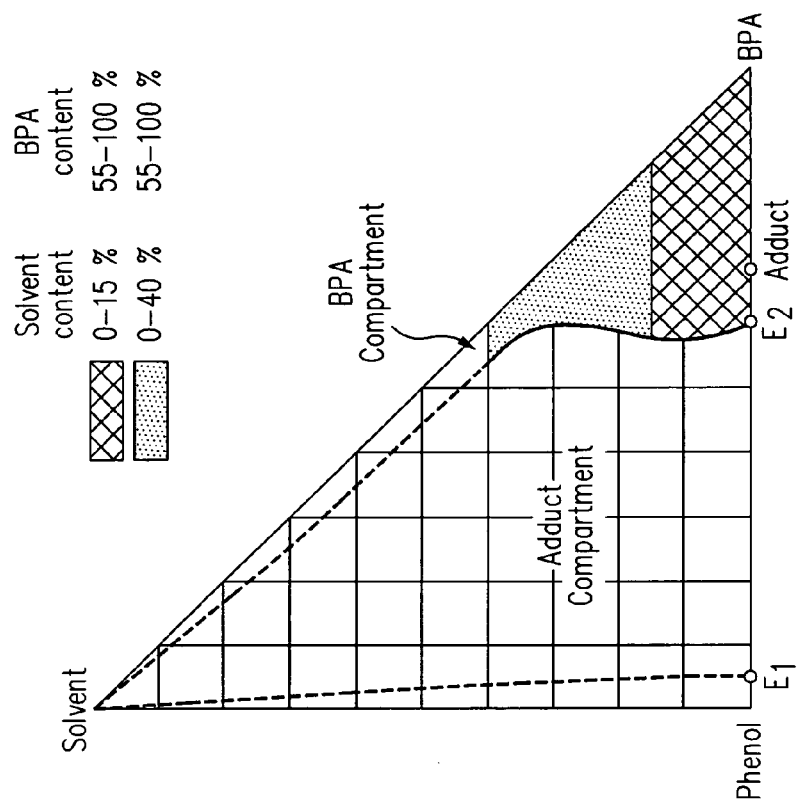
FIG. 4 is a polythermal projection of the phase equilibrium diagram for the ternary system of Bisphenol-A, Phenol and Solvent showing the regions of composition of the crystallizer feed, which are preferable from the point of view of process operation according to one embodiment of the present invention where the solvent is comprised of a mixture of Acetone and Water.

Referring specifically to FIG. 4, the projection of a polythermal phase diagram of the ternary system of Phenol, Bisphenol-A and Solvent is shown. FIG. 4 is used to illustrate the crystallization of Bisphenol-A. The components exhibit a phase behavior which establishes at least two regions or compartments in the phase diagram, an adduct phase compartment and a pure solid Bisphenol-A phase compartment. A solvent compartment is also present, but is not discussed in detail since it is not of significant interest to the teaching of the present invention. According to the present invention the location of the boundary of the compartment, and thus the size of the adduct compartment and the Bisphenol-A compartments, are selectively controlled or manipulated by adjusting the composition of the solvent, or in the case where the solvent is a mixture, such as of Acetone and Water, by adjusting the concentration ratio of the two solvent components. In this invention, the composition of the feed stream to the crystallization stage and hence the location of the feed point on the phase diagram is adjusted so that the feed composition lies in the Bisphenol-A region.

Preferably, the feed stream composition is such that it lies in the shaded area shown in FIG. 4. In this example the concentration of solvent in the crystallizer feed is in the range of about 0 to 40 wt. % and the concentration of Bisphenol-A in the feed is in the range of about 55 to 100 wt. %. More preferably, the concentration of solvent in the feed is in the range of about 0 to 15 wt. % and the concentration of Bisphenol-A in the feed is in the range of about 55 to 100 wt. %.

Figure 5:
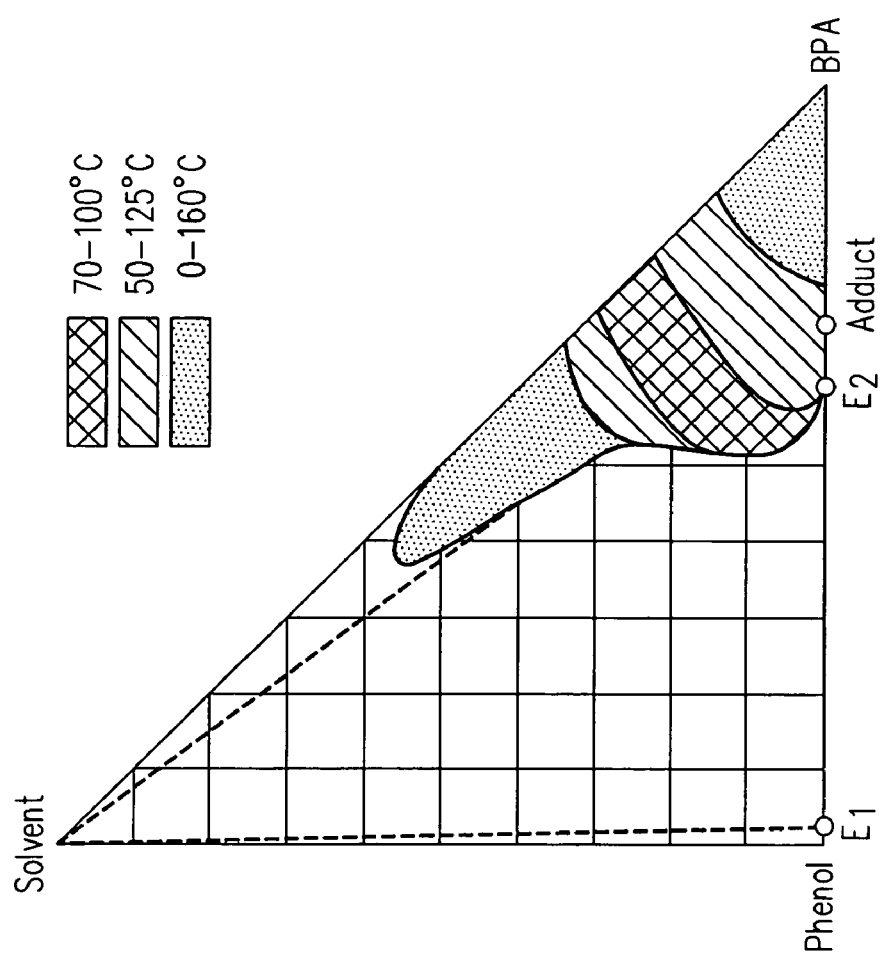
FIG. 5 is a polythermal projection of the phase equilibrium diagram for the ternary system of Bisphenol-A, Phenol and Solvent showing the temperature ranges and regions of composition inside the crystallizer, which are preferable from the point of view of process operation according to one embodiment of the present invention where the solvent is comprised of a mixture of Acetone and Water.

As pointed out earlier, composition of the outlet of the BPA crystallizer (also known as the mother liquor) will also lie in the BPA compartment in the ternary phase diagram. The location of this point depends on the amount of BPA recovered in the crystallizer, which in turn depends on the operating conditions of the crystallizer, such as operation temperature for a cooling crystallizer. The preferred area of the crystallizer outlet composition is depicted as a shaded area in FIG. 5, based on the temperature of operation of a cooling crystallizer. FIG. 5 shows the region of the Phenol-BPA-Solvent composition space where the Bisphenol-A crystallizer operates in a temperature range between approximately 0 and 160° C., more preferably in the range of 50 to 125° C., and most preferably in the range of 70 to 100° C.

Those of ordinary skill in the art will recognize that the size of the compartments in FIGS. 4 and 5 may move somewhat if impurities or other components are present in the product solution.

It is important to note that although the feed solution to the BPA crystallizer stage is comprised of a multitude of components, including unreacted reactants and byproducts of the reaction, for process synthesis purposes it is sufficient to consider only the principal components. The principal components are Phenol, Bisphenol-A and the solvent (a pseudo-component generically referred to as the solvent). The solvent components may already be present in the product solution available from the reaction step, such as unreacted Acetone and the Water formed in the reaction, or may be introduced into the system before the crystallization step. The system of Phenol, Bisphenol-A and the solvent is treated as a ternary phase equilibrium system whose phase behavior will depend on the exact nature of the solvent. In a preferred embodiment the solvent is comprised of a mixture of Acetone and Water in varying proportions.

Calculating Phase Diagrams

Given the teaching of the present invention, ternary phase equilibrium diagrams for different solvent compositions and/or concentration ratios may be created by those of ordinary skill in the art without undue experimentation. For example, computer simulation programs and thermodynamic databases may be used to develop the approximate location of the boundary of the bisphenol- and adduct compartments for different pure solvents and/or solvent mixtures with different concentration ratios. The boundary between the adduct compartment and the Bisphenol-A compartment is the trajectory of incongruent melting points. The incongruent melting point is the location where both Bisphenol-A and adduct solid coexist. The maximum recovery of Bisphenol-A is the maximum amount of Bisphenol-A solid that can be recovered before adduct solid appears (or coexists with the Bisphenol-A solid). It should be noted that the polythermal phase diagrams shown herein are not to scale but are presented here for schematic illustration purposes.

More specifically, the establishment of a thermodynamic model for the multi-component solid liquid equilibrium uses both theoretical calculation and experimental data for the model verification. Those of ordinary skill in the art can develop such thermodynamic models using known principles and tools.

The physical properties of the each component in the feed solution to the crystallizer such as the heat of fusion, melting point, and heat capacity are used to establish the thermodynamic model which describes the equilibrium relationship between the components as a function of temperature. The theory for the activity coefficient is well developed, and a computer software program providing numerical methods for estimating the equilibrium relationships between the components is typically used. The binary interaction parameters among the components in the solution are either estimated or determined from experimental data. Examples of suitable commercially available software programs for thermodynamic model establishment include PropertiesPlus from Aspen Technology Inc., HYPROP III from Hyprotech, and ProPred from CAPEC at the Technical University of Denmark. The thermodynamic model is for the calculation of the concentration of the component when it is saturated and is a function of temperature and concentration. Since the effect of pressure on the saturation is not very significant in the pressure range considered, the pressure effect is not taken into account in this thermodynamic model; however, the analysis may be extended to consider the pressure effect if desired.

The region of the Bisphenol-A compartment can be determined if the trajectory of the incongruent melting points can be determined. Since the incongruent melting point occurs when both adduct and Bisphenol-A are saturated, this trajectory can be calculated from the thermodynamic model by those of ordinary skill in the art. The regions for the Phenol compartment can be calculated once the trajectory of the eutectic point between Phenol and adduct is determined. This trajectory can be also calculated by those of ordinary skill in the art from the thermodynamic model since the eutectic points occur when both Phenol and adduct are saturated. The region between the Phenol compartment and the Bisphenol-A compartment in the concentration diagram is the adduct compartment. The temperature along the trajectory of incongruent melting points and the trajectory of the eutectic points is also determined from the thermodynamic model by known techniques. Further detailed description regarding the development of the phase diagrams may be found in pending U.S. patent application Ser. No. 10/099,227 filed on Mar. 13, 2002, the entire disclosure of which is expressly incorporated herein by reference.

System (Process Configuration) of the Present Invention

Figure 6:
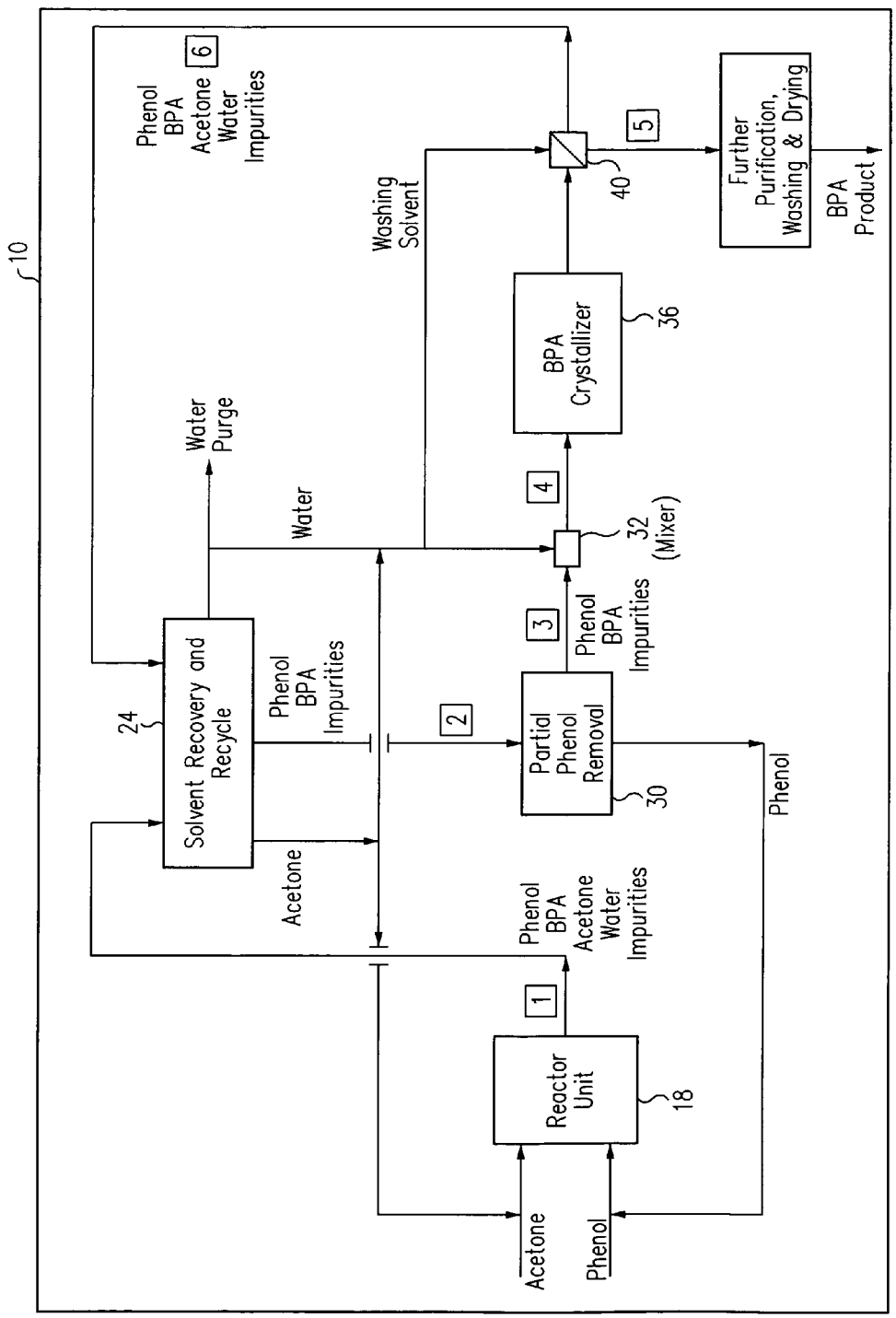
FIG. 6 is a schematic diagram illustrating a process configuration for producing Bisphenol-A according to one embodiment of the system of the present invention.

Of particular advantage, the present invention provides a process for producing Bisphenol-A by direct crystallization in a single crystallization stage. One embodiment of the system of the present invention is illustrated in FIG. 6 In general, the system 10 is comprised of a reactor unit 18, a solvent recovery unit 24, a partial Phenol removal unit 30, and a Bisphenol-A crystallizer stage 36. Upstream of the BPA crystallizer stage 36, a mixing unit or mixer 32 is employed to adjust the composition of the solvent in the product solution prior to the crystallizer. Downstream of the crystallizer stage 36, a solid/liquid (S/L) separator 40 may be employed to separate the BPA crystals from the remaining solution. The Bisphenol-A crystals produced from the crystallizer stage 36 may be further processed by washing, followed by drying or further purification methods such as recrystallization and the like, although not shown.

To form Bisphenol-A, Phenol (preferable purified and preferably in stoichiometric excess) and Acetone are conveyed to the reactor unit 18 where a condensation reaction is carried out. Reactor unit 18 is preferably a fixed bed reactor, filled with an acid catalyst, preferably an Ion Exchange Resin (IER) type of catalyst. The reactants are passed through the fixed bed of catalyst to produce a product solution in the liquid phase. The product solution includes Bisphenol-A, unreacted reactants such as excess Phenol and/or Acetone, by-products of the reaction (such as Water) and impurities such as isomers, analogs and homologs. The condensation reaction may be carried out at a temperature in the range of about 45° C. to 120° C., and more preferably in the range of about 50° C. to 100° C. with about 75° C. being most preferred. The reaction pressure is in the range of about 1 to 8 bar, more preferably about 1 to 6 bar, with a reaction pressure of about 4.4 bar being most preferred.

Figure 8B:
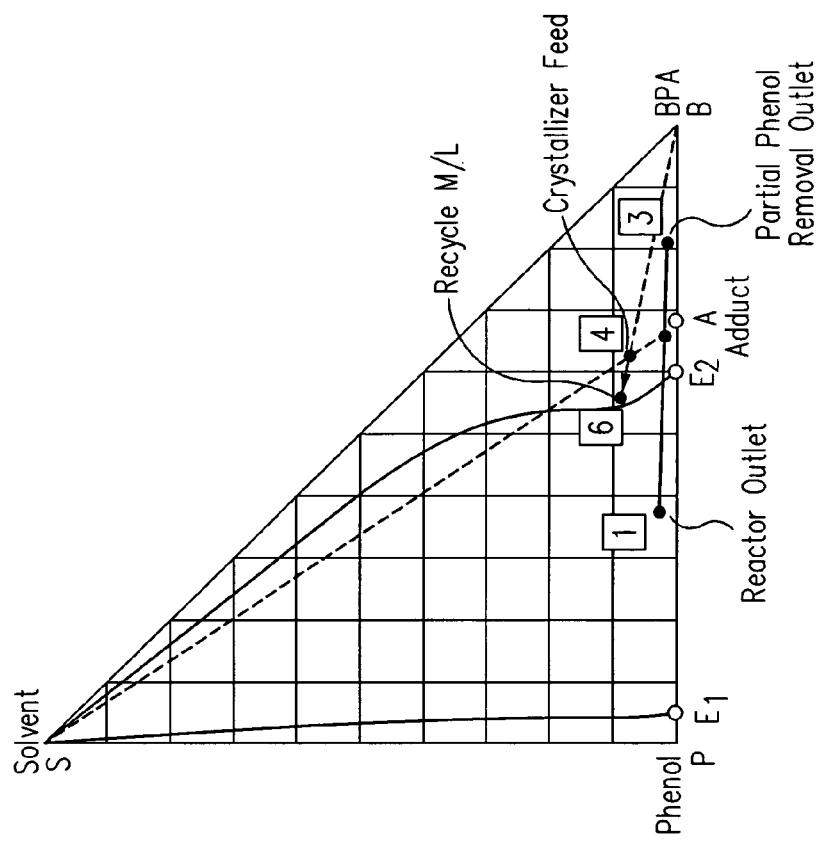
FIG. 8(b) is the polythermal projection of the phase equilibrium diagram for the ternary system of Bisphenol-A, Phenol and Solvent showing the composition of the process streams for the system described in FIG. 7.
Figure 8A:
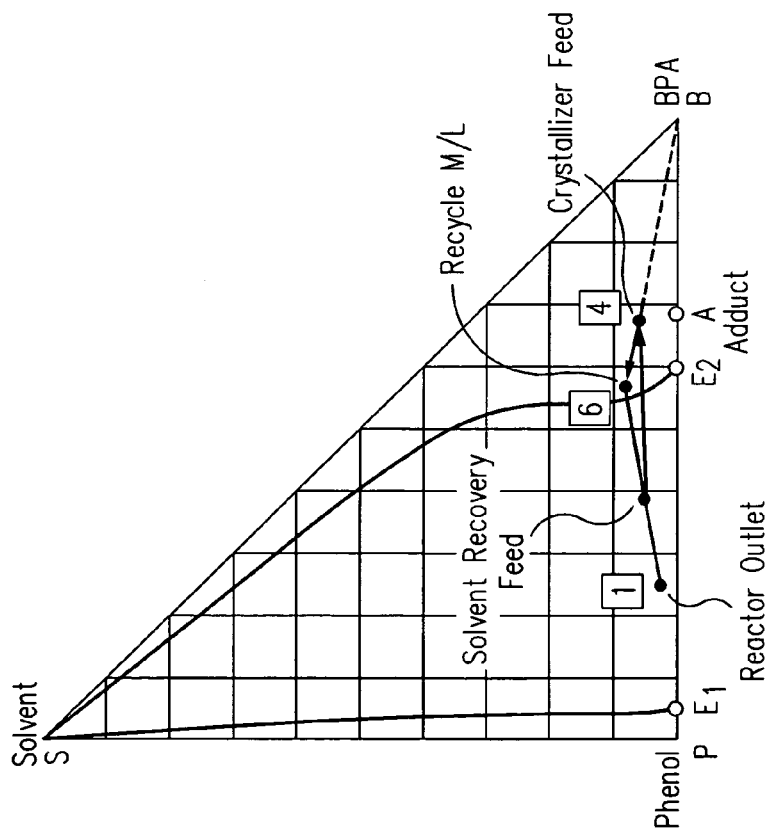
FIG. 8(a) is the polythermal projection of the phase equilibrium diagram for the ternary system of Bisphenol-A, Phenol and Solvent showing the composition of the process streams for the system described in FIG. 6.

The product solution following the reaction is identified as Stream (or product stream) number 1 (streams are depicted in a box) on FIG. 6. The composition of this stream on an impurity free basis can be plotted on a polythermal phase diagram of the ternary system comprised of Bisphenol-A, Phenol, and Solvent, as shown in FIG. 8(*a*). Ordinarily, the feed to the reactor unit 18 contains Phenol in excess of the stoichiometric requirement of two moles of Phenol for every mole of Acetone fed to the reactor. Thus, ordinarily, the product solution following the reaction contains a significant amount of unreacted Phenol, and hence is located outside the BPA crystallization compartment in the ternary polythermal phase diagram The composition of Stream 1 is identified by point 1 in FIG. 8(*a*).

Following the reaction, the composition of the product solution is adjusted so as to place it within the Bisphenol-A crystallization compartment, so that BPA may be recovered upon crystallization. The composition of the product solution may be adjusted in several ways. The product solution may be mixed with a recycle stream rich in BPA. Alternatively, a part of the Phenol and/or the solvent from the product solution may be removed to increase the concentration of BPA in the product solution. In case the reactor outlet is already located in the BPA crystallization compartment, such steps for reducing the concentration of Phenol in the product solution may not be required.

Additionally, at this stage, the solvent composition in the product solution may also be adjusted by either addition or removal of one or more solvent components from the product solution.

Figure 7:
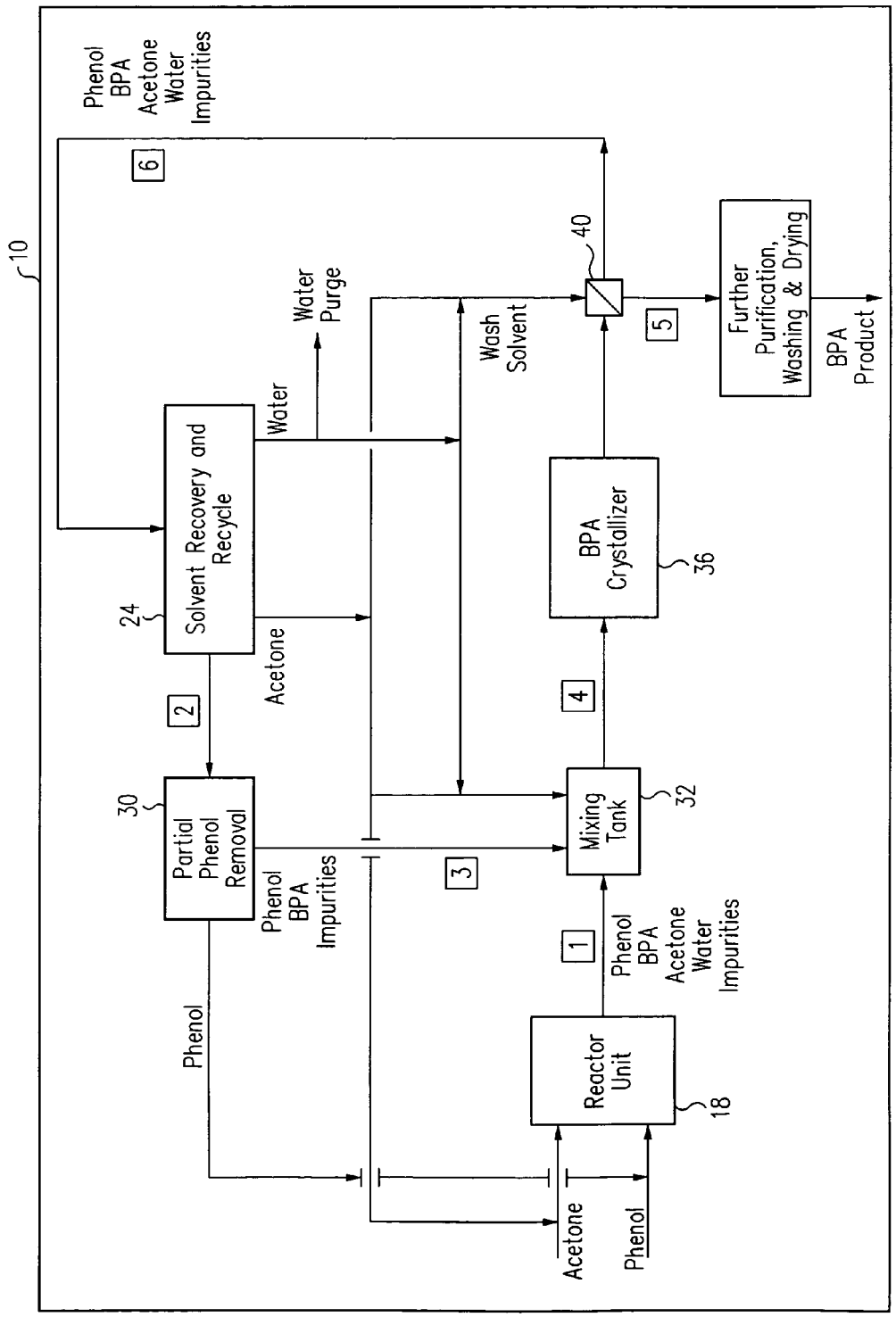
FIG. 7 is a schematic diagram illustrating a process configuration for producing Bisphenol-A according to a second embodiment of the system of the present invention.

Any one of, or more usually, a combination of the above steps may be taken in order to adjust the composition of the product solution, such that it lies in the desired Bisphenol-A crystallization compartment prior to the crystallization, and contains Solvent in the desired amount and composition. The sequence in which the above steps are arranged may also differ, leading to somewhat different process configurations. Although two such different process configurations are shown in FIGS. 6 and 7, the invention is not limited to these specific process configurations, and those of ordinary skill in the art will recognize that other process configurations may be used within the scope of the teaching of the present invention.

According to one embodiment of the system of the present invention as shown in FIG. 6, the feed stream to the Bisphenol-A crystallizer stage 36 is identified as stream 4. The corresponding location of the crystallizer feed composition is shown by point 4 on the projection of the polythermal phase diagram in FIG. 8(*a*). In this exemplary embodiment the composition of the product stream is adjusted from a composition corresponding to point 1 on FIG. 8(*a*) to a composition corresponding to point 4 by mixing with a recycle stream as well as the addition and removal of various components as described below. Following the reaction, the product solution (Stream 1) and the recycled mother liquor from the BPA crystallizer (Stream 6), are together fed to the Solvent recovery unit 24. The Solvent recovery unit may use separation methods such as distillation and the like, in order to recover the solvent components, in part or in full, from the product solution. The resulting product mixture is richer in BPA and leaner in the solvent components than before. The solvent stream(s) recovered from the solvent recovery unit may be recycled in part to the reactor, and/or may be independently added to the mixing unit 32 in order to adjust the composition of the mixture prior to the BPA crystallization step. The solvent components may also be used to wash the BPA crystals in a washing step (not shown) downstream to the crystallization step.

Figure 10:
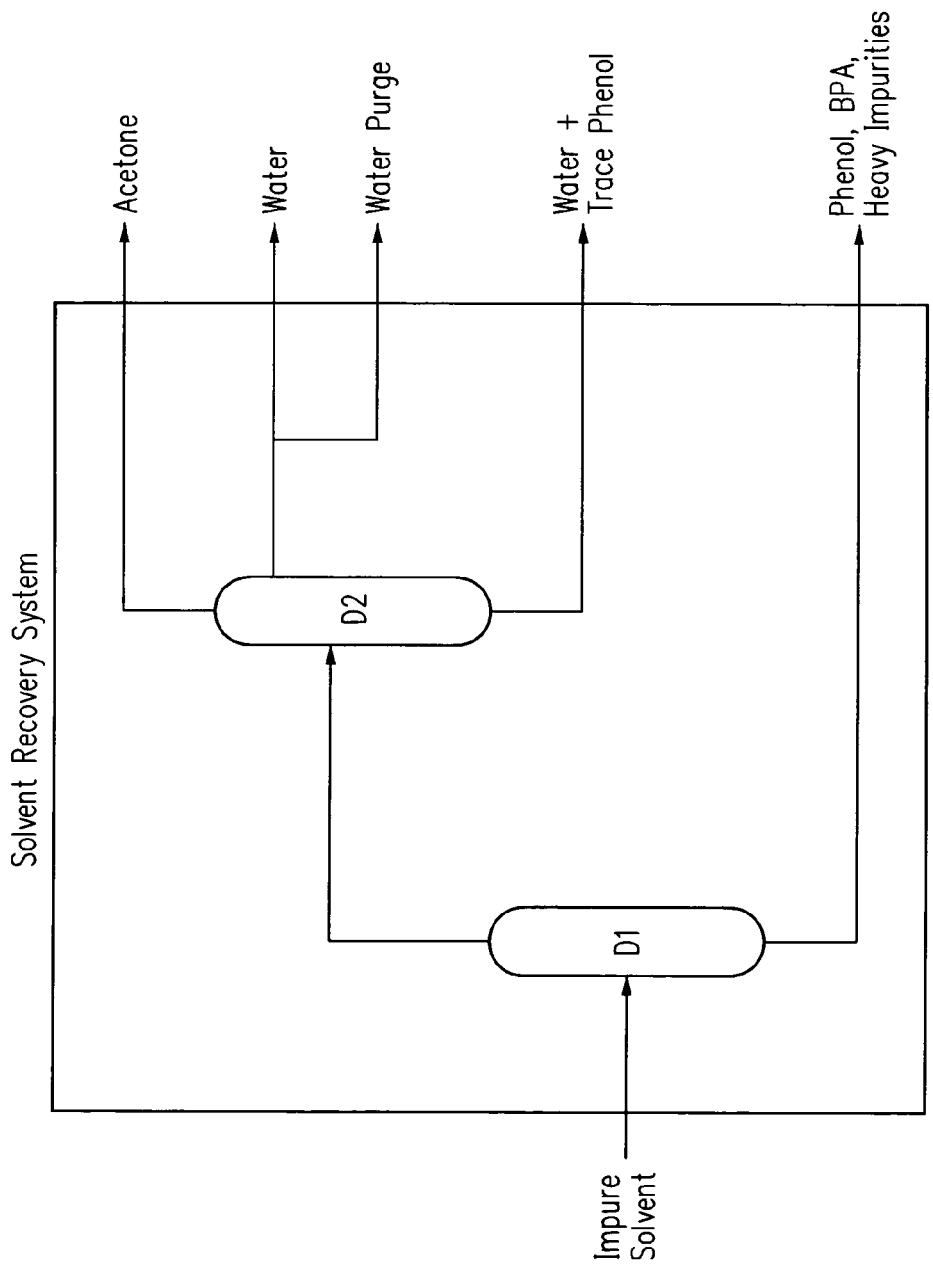
FIG. 10 is a schematic illustration showing the details of the Solvent recovery system which may be employed in the system described in FIG. 6 or FIG. 7.

In the preferred embodiment where the solvent is comprised of a mixture of Acetone and Water, the Solvent recovery unit 24 is used to recover a pure Acetone and a pure Water stream from the product solution. A schematic illustration of the details of the solvent recovery system which may be used in this case is shown in FIG. 10. A part of the Acetone recovered from the solvent recovery unit is recycled to the reactor unit 18. A part of the Water and Acetone are combined with the product stream in the mixing unit 32, to obtain the desired amount and composition of solvent in the solution prior to crystallization. Some amount of Acetone and Water may also be used as a wash solvent in the crystal washing step (not shown) subsequent to crystallization.

Following the solvent recovery unit 24, the product stream identified as Stream 2 in FIG. 6, is fed to a partial Phenol recovery unit 30, to remove a part of the Phenol present in the product mixture, if required The partial Phenol recovery unit 30 may employ separation methods such as a distillation column. A majority of the Phenol recovered here may be recycled back to the reactor unit 18, while a part may be mixed with solvent to provide a wash solvent for the BPA crystals subsequent to crystallization. The resulting product stream (Stream 3) after the partial Phenol removal is richer in Bisphenol-A and may contain no more than 40% Phenol by weight. A part of the product stream may be optionally sent to an isomerization unit or a tar cracking unit (not shown) in order to convert the BPA isomers to BPA, and to purge a part of the heavy impurities.

Following the partial Phenol recovery, the product solution containing BPA in excess of 55 wt. % is conveyed to a mixing unit 32, where the amount and composition of the solvent in the mixture may be adjusted prior to the crystallization step. The choice of the amount and composition of solvent in the crystallizer feed stream is important because it affects the per-pass recovery of the solid product from the crystallizer, as well as the operating conditions of the crystallizer, such as its temperature, rate of evaporation of solvent, or residence time.

In the preferred embodiment where the solvent comprises of a mixture of Acetone and Water, the two solvent components recovered from the solvent recovery unit 24, may be mixed in various proportions to the product mixture, to yield a crystallizer feed stream with the desired amount and composition of Solvent such that it lies in the Bisphenol-A crystallization compartment in the phase diagram. From point of view of crystallizer operation, the preferable range of the solvent content in the crystallizer feed may be from 0–40% by weight, and more preferably from 0–15% by weight. The preferable range of BPA concentration in the crystallizer feed is from about 55 to 100 wt. %. The remaining part is mostly Phenol, along with some amount of impurities. In this exemplary embodiment, the crystallizer feed stream is identified by point 4 on FIG. 8(*a*) and is seen to lie in the BPA compartment.

Having achieved the desired feed composition for Bisphenol-A crystallization, the solution is fed to the BPA crystallizer stage 36, where substantially pure Bisphenol-A is recovered in crystal form. The BPA crystallizer stage 36 may be comprised of one or more crystallization units. Crystallizers are known in the art, and typically provide crystallization by indirect or external cooling such as with heat exchanges or circulating cooling medium. Crystallization may also be provided by pressure reduction, or by a combination of external heating and pressure reduction. In one example, the solution is cooled in the BPA crystallizer 36 to a temperature in the range of 0° C. to 160° C., more preferably to a temperature in the range of about 50° C. to 125° C. Most preferably, the solution is cooled to a temperature in the range of 70° C. to 100° C. The operating pressure range depends on the type of solvent used and the crystallizer temperature, and the pressure should be selected such that the vapor fraction in the crystallizer is low or minimized. The BPA crystallizer is typically operated at a pressure in the range of about 0.1 bar to 6 bar. In an exemplary embodiment, where a mixture of Acetone and Water is employed as the solvent the pressure in the BPA crystallizer 36 is in the range of about 0.5 bar to 5 bar, with about 3 bar being most preferred to maximize the liquid fraction in the crystallizer.

As crystallization takes place, solid Bisphenol-A is formed. The residence time in the BPA crystallizer 36 is in the range of about 1 to 10 hours ideally, more preferably in the range of about 2 to 5 hours. It should be understood that the optimum residence time is a function of the crystal growth rate in a given solvent, and thus the optimum residence time will vary depending on the type of solvent employed.

The solid BPA is separated from the remaining solution (referred to as mother liquor or M/L) in the solid/liquid separator 40, employed downstream of the BPA crystallizer. Any suitable type of S/L separator as known in the art may be used such as a centrifuge or filtration device, or the like. Upon separation the solid BPA will have a composition corresponding to point B in FIG. 8(*a*), whereas the mother liquor will have a composition corresponding to point 6. The mother liquor corresponding to Stream 6 in FIG. 6 is conveyed to the solvent recovery unit 24 together with the product stream coming out of the reactor, to recover and recycle the solvent. The Bisphenol-A crystals are washed preferably with the solvent in S/L separator 40 to remove any residual mother liquor. The BPA crystals are then dried in a suitable drying unit (not shown), or subjected to further purification steps if desired. These include re-dissolution of the BPA crystals in a suitable solvent, re-crystallization at a suitable temperature, followed by washing and drying, in order to obtain the desired purity.

It should be made clear that although the above description of the present invention describes crystallization primarily by cooling, the present invention may employ other types of crystallization methods such as evaporative crystallization, and the like.

Variations of the process configuration illustrated in FIG. 6 are possible, depending on the sequence in which the process steps are undertaken. An alternative embodiment of the system of the present invention is schematically illustrated in FIG. 7. Here, the product stream after the reaction is not sent to the solvent recovery unit 24. Instead the product stream from the reactor unit 18 is directly sent to the BPA crystallization stage 36, after adjusting the composition of the stream in the mixing unit or tank 32, such that it lies in the BPA crystallization compartment prior to crystallization. The product stream after the reaction is identified as Stream 1 (again, streams are depicted in a box) in FIG. 7. The composition of this stream on an impurity free basis can be plotted on a polythermal ternary projection as shown in FIG. 8(*b*), where it is identified by point 1. In this example embodiment, the composition of the product stream corresponding to point 1 on FIG. 8(*b*) is adjusted to the composition corresponding to point 4, by various means prior to crystallization, as discussed below.

Following the reaction, the product stream (Stream 1) is sent to the mixing unit 32 where it is combined with the BPA rich recycle stream (Stream 3 in FIG. 7) from the partial Phenol removal unit 30. Also, the amount and composition of the solvent in the mixture is adjusted by mixing an appropriate solvent stream from the solvent recovery unit 24 in order to yield the crystallizer feed stream shown as Stream 4 in FIGS. 7 and 8(*b*). The preferable range of the solvent content in the crystallizer feed may be from 0–40% by weight, and more preferably from 0–15% by weight. The preferable range of BPA in the crystallizer feed is from about 55 to 100 wt. %.

Having achieved the desired feed composition for Bisphenol-A crystallization, the solution is fed to the BPA crystallizer stage 36, where substantially pure Bisphenol-A is recovered in crystal form. The solid BPA is separated from the remaining solution (referred to as mother liquor or M/L) in the solid/liquid separator 40, employed downstream of the BPA crystallizer. The mother liquor is conveyed to the solvent recovery unit 24 to recover and recycle the solvent. The Bisphenol-A crystals are washed preferably with the solvent in S/L separator 40 to remove any residual mother liquor.

Figure 9:
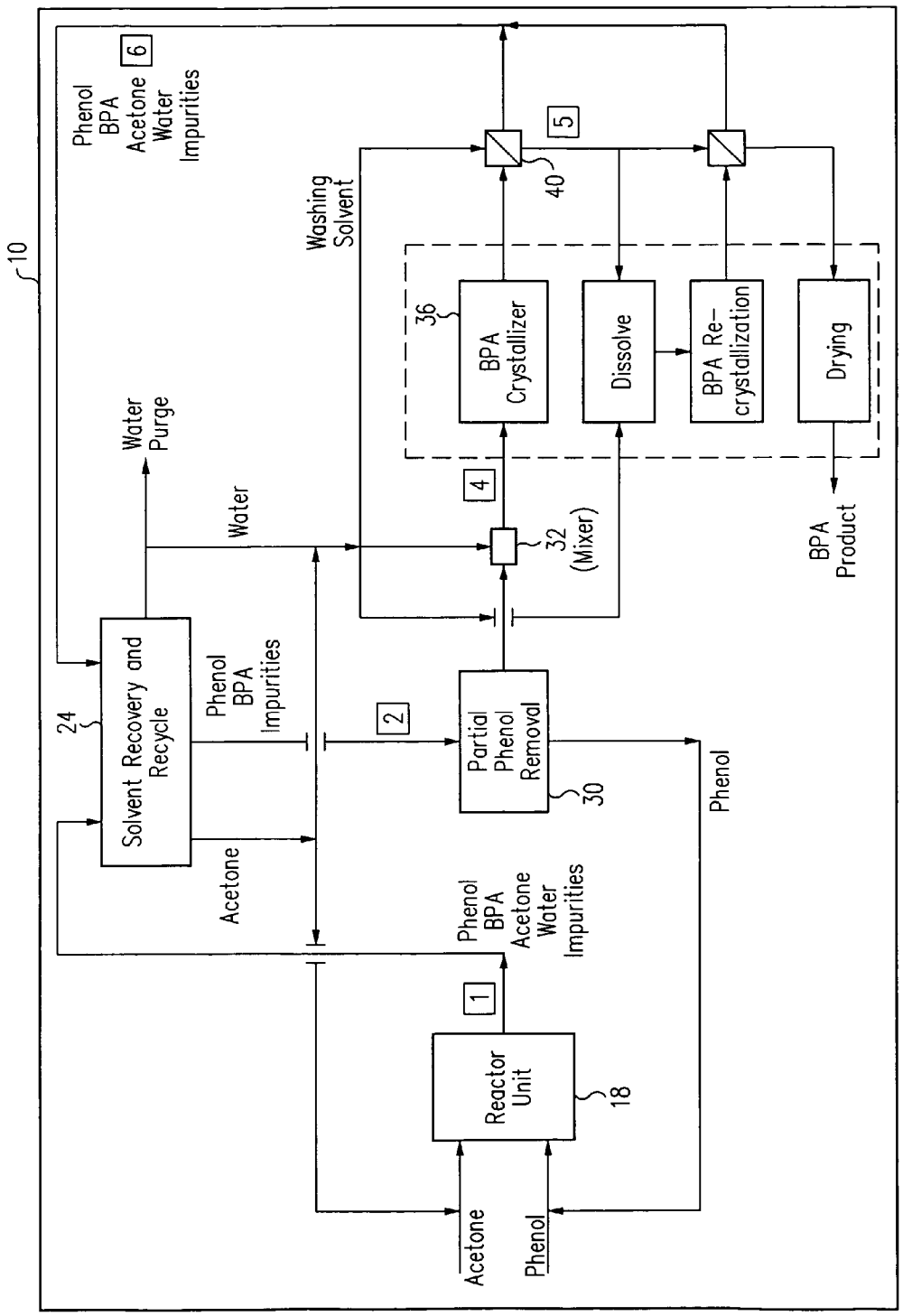
FIG. 9 is a schematic diagram illustrating a process configuration for producing Bisphenol-A which includes a recrystallization step after the primary BPA crystallization.

The BPA crystals are then dried in a suitable drying unit (not shown), or subjected to further purification steps if desired to obtain BPA of a higher purity. These include re-dissolution of the BPA crystals in a suitable solvent, re-crystallization at a suitable temperature, followed by washing and drying, in order to obtain the desired purity. In this instance the BPA crystallizer stage will consist of more than one crystallizer unit providing for the recystallization steps, such as that illustrated in FIG. 9 which shows a schematic of the process of FIG. 6 with a the recrystallization units shown in the BPA crystallization stage.

Those of ordinary skill in the art will recognize the significant advantages provided by the present invention. The present invention provides a system wherein numerous routes, system designs and variation in sequence of operation steps can be taken in order to adjust the composition of the product stream after the reaction so that it lies in the Bisphenol-A crystallization compartment prior to the crystallization stage. Since Bisphenol-A crystals can be recovered directly in the crystallizer stage, the intermediate steps for the recovery of the adduct, and the complex and costly dephenolation steps for removal of Phenol from the adduct as required by the prior art processes are absent.

EXPERIMENTAL

Simulated experiments are provided below to further illustrate the system and method of the present invention. These simulated experiments are provided for illustration purposes only and are not intended to limit the scope of the invention in any way.

EXAMPLE 1

Stream Composition from Process Configuration 1

Simulated examples showing typical stream compositions for the major solution streams are provided, corresponding to one process configuration resulting from the system of the present invention as shown in FIG. 6. Solution stream compositions shown in Table 1 below are in wt. %, on an impurity free basis. Note, that impurities are typically present at the inlet and outlet of the reactor, however they are considered to be minimal. Examples of typical impurities, include but are not limited to: by-products such as 2,4-Bisphenol-A, Trisphenol, chromans, IPP dimers, and other higher condensation products. In this example, the solvent is comprised of a mixture of Acetone and Water. The overall Phenol to Acetone ratio in the fresh feed is 2 on a mole basis. The Phenol to Acetone ratio in the feed to the reactor is 11.5 on a mole basis. The high Phenol to Acetone ratio leads to a high per pass Acetone conversion of 99.6%.

TABLE 1

| Component | Reactor Feed wt. % | Reactor Outlet wt. % | Feed to Crystallization Stage wt. % | Mother Liquor from Crystallization Stage wt. % |
|---|---|---|---|---|
| Phenol | 88.42 | 73.16 | 28.18 | 35.11 |
| BPA | 6.85 | 25.36 | 65.77 | 57.34 |
| Acetone | 4.72 | 0.02 | 1.42 | 1.78 |
| Water | 0.01 | 1.46 | 4.63 | 5.77 |
| Total | 100.00 | 100.00 | 100.00 | 100.00 |

As shown, the composition of the product solution at the feed to the crystallization stage is selectively provided such that pure Bisphenol-A crystals are formed during crystallization. The Bisphenol-A recovery in the crystallizer is 30.4% on a weight basis.

EXAMPLE 2

Stream Composition from Process Configuration 2

This simulated example shows the typical stream compositions for the major solution streams, for another process configuration resulting from the system of the present invention as shown in FIG. 7. Solution stream compositions shown in Table 2 below are in wt. %, on an impurity free basis. As before, the solvent in this example is comprised of a mixture of Acetone and Water. The overall Phenol to Acetone ratio in the fresh feed is 2 on a mole basis. The Phenol to Acetone ratio in the feed to the reactor is 9.85 on a mole basis, the per pass Acetone conversion being 98.4%.

TABLE 2

| Component | Reactor Feed wt. % | Reactor Outlet wt. % | Feed to Crystallization Stage wt. % | Mother Liquor from Crystallization Stage wt. % |
|---|---|---|---|---|
| Phenol | 81.07 | 64.93 | 33.75 | 38.57 |
| BPA | 13.84 | 33.42 | 58.80 | 55.55 |
| Acetone | 5.08 | 0.01 | 3.07 | 3.31 |
| Water | 0.01 | 1.54 | 2.38 | 2.57 |
| Total | 100.00 | 100.00 | 100.00 | 100.00 |

As shown, the composition of the product solution at the feed to the crystallization stage is selectively provided such that pure Bisphenol-A crystals are formed during crystallization. The Bisphenol-A recovery in the crystallizer is 11.5% on a weight basis.

EXAMPLE 3

Summary of Process Operation at Different Operating Conditions

The above examples showed the typical process stream compositions at a chosen set of operating conditions for each of the two process configurations. In practice, the process has a number of process operating variables, or handles which can be changed to vary the process performance. Markedly different process stream compositions can be obtained when the same process is carried out with a different choice of the process handles. For the process configurations depicted in FIGS. 6 and 7, the process handles include, but are not limited to: the amount of catalyst in the reactor unit 18, the flow velocity of the reactants through the reactor unit, the Phenol to Acetone ratio at the reactor inlet, the fraction of Solvent recovered by the solvent recovery unit 24, the fraction of recovered Acetone solvent recycled back to the reactor, the fraction of Phenol removed by the Phenol removal unit 30, and the operation temperature, the cooling rate, or the evaporation rate in the Bisphenol-A crystallizer unit 36.

Several simulated examples with a different choice of key process variables were carried out. A summary of results from the case studies is reported below in Table 3. The results reported include, the Phenol to Acetone ratio in the reactor feed stream, the per pass Acetone conversion in the reactor, the per pass recovery of Bisphenol-A in the crystallization stage, and the total solvent content and the solvent composition in the crystallizer feed. Also noted in the table below is the load on the solvent recovery system 24, which is signified by the amount in kg of solvent (here, Acetone and Water) being recovered and recycled in the process, per kg of Bisphenol-A produced. Similarly, the load on the partial Phenol recovery system is reported, this being signified by the kg of Phenol being removed in unit 30, per kg of BPA produced.

TABLE 3

| Case | Phenol to Acetone ratio in reactor feed | Per pass Acetone conversion % | Per pass BPA recovery in crystallizer % | Solvent content in crystallizer wt % | Crystallizer Solvent composition | | BPA in reactor feed (wt. %) | Solvent removal in unit 24 (kg/kg BPA) | Phenol removal in unit 30 (kg/kg BPA) |
|---|---|---|---|---|---|---|---|---|---|
| | | | | | Acetone wt. % | Water wt. % | | | |
| Process Configuration 1 (FIG. 6) | | | | | | | | | |
| 3.1 | 11.54 | 99.62 | 30.00 | 6.06 | 23.53 | 76.47 | 6.85 | 0.39 | 3.79 |
| 3.2 | 11.16 | 87.02 | 45.00 | 9.88 | 49.83 | 50.17 | 4.24 | 0.42 | 4.40 |
| 3.3 | 7.28 | 92.13 | 25.00 | 5.06 | 64.39 | 35.61 | 11.17 | 0.41 | 2.24 |
| 3.4 | 15.65 | 99.78 | 55.00 | 10.74 | 9.98 | 90.02 | 0.55 | 0.35 | 5.63 |
| 3.5 | 11.78 | 99.10 | 21.00 | 21.94 | 57.53 | 42.47 | 9.30 | 1.75 | 3.95 |
| Process Configuration 2 (FIG. 7) | | | | | | | | | |
| 3.6 | 9.85 | 98.02 | 12.43 | 5.45 | 56.0 | 44.0 | 13.85 | 0.75 | 3.13 |
| 3.7 | 10.72 | 97.90 | 11.58 | 4.39 | 12.0 | 88.0 | 0.00 | 0.65 | 3.69 |
| 3.8 | 5.80 | 88.87 | 21.78 | 7.29 | 15.0 | 85.0 | 19.45 | 0.56 | 1.68 |
| 3.9 | 6.25 | 90.62 | 16.48 | 7.78 | 33.0 | 67.0 | 1.60 | 0.79 | 2.00 |

In summary, it is shown that the present invention provides a powerful tool wherein numerous routes, system design and operating conditions can be manipulated for selective control of the process. In particular, the composition of the feed to the crystallizer can be adjusted using various means and methods described above so that it lies in the Bisphenol-A crystallization compartment prior to the crystallization stage.

Process variables that can be manipulated to achieve a desired target include: changing the type and composition of solvent to change the phase behavior; adding or removing any one of or combination of Phenol, Bisphenol-A, or Solvent in order to change the composition of the product mixture so as to bring it within the BPA crystallization compartment; control of the condensation reaction coupled with control of the process operation conditions to achieve the same; an alteration in the sequence of process operations to achieve the same target; and controlling the recovery of solid in the crystallizer by controlling the temperature once the location of the crystallizer feed in the phase diagram is known.

Of significant advantage, the system and method of the present invention provides for the direct crystallization of Bisphenol-A from the product solution following the reaction, without the need for the intermediate step of recovering the adduct of Phenol and Bisphenol-A, as described in the prior art. This leads to a considerable reduction in the number of processing steps required to obtain pure BPA, thereby reducing capital and energy costs.

Of further advantage, since the intermediate adduct crystallization step is absent, the system and process of the present invention does not require a complete removal of Phenol from the adduct, usually carried out in expensive steps such as a dephenolation unit. As discussed earlier, conventional prior art methods of recovering Bisphenol-A from the adduct require melting the adduct and removing almost all of the Phenol by evaporation for example in a wiped film evaporator, and the recovering Bisphenol-A by melt or solution crystallization. The process of the present invention requires only a partial removal of Phenol from the product solution. Furthermore, this partial Phenol removal is carried out at a much higher concentration of Phenol, and is hence much cheaper, than that in the prior art processes.

In the prior art processes, solid Bisphenol-A product is obtained from molten Bisphenol-A by a prilling process. In the present invention, high quality Bisphenol-A is recovered in the crystal form directly from solution, which eliminates the need for expensive solids formation units such as a prilling tower.

The process of the present invention eliminates the need for all the intermediate process steps for recovering and purifying the adduct, and then recovering the Bisphenol-A from the adduct. This process therefore is significantly simpler to build and operate and provides considerable savings in capital cost and energy consumption.

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

We claim:

1. A system for producing Bisphenol-A, comprising:
   a reactor unit wherein a product stream is produced including at least Bisphenol-A and Phenol;
   a mixer/separator unit, said mixer/separator unit being configured to selectively add solvent to the product stream wherein the composition of the product stream exhibits a phase equilibrium relationship such that Bisphenol-A crystals are formed during crystallization; and
   a BPA crystallizer stage, the crystallizer stage receiving the product stream and wherein substantially pure Bisphenol-A crystals are produced directly upon crystallization in the BPA crystallizer stage, without prior adduct crystallization.

2. The system of claim 1 wherein the mixer/separator unit is located upstream of the BPA stage crystallizer.

3. The system of claim 1 further comprising:
   a solvent recovery unit configured to recover solvent used in the system, the solvent recovery unit being coupled to at least any one, or more of, the reactor unit, mixer/separator or partial phenol removal unit to selectively adjust the composition of the product stream.

4. The system of claim 1 further comprising a partial phenol removal unit configured to adjust the composition of phenol in the product stream such that the product stream when fed to the BPA crystallizer stage does not contain more than 40 wt. % phenol.

5. The system of claim 1 where the BPA crystallizer stage is comprised of one or more crystallizer units.

6. A system for producing Bisphenol-A, comprising:
   a reactor unit wherein a product stream is produced including at least Bisphenol-A and Phenol;
   a partial phenol removal unit:
   a mixer/separator unit, the mixer/separator unit receiving the product stream from the reactor unit or the partial phenol removal unit and being configured to selectively adjust the composition of the product stream by mixing with one or more recycle streams; and
   a BPA crystallizer stage, the crystallizer stage receiving the product stream from the mixer/separator unit and whereupon crystallization substantially pure Bisphenol-A crystals are produced directly upon crystallization in the BPA crystallizer stage, without prior adduct crystallization.

7. The system of claim 6 further comprising a solvent recovery unit, wherein both of said partial phenol removal unit and said solvent recovery unit produce recycle streams, and where one or more of the recycle streams are conveyed to the mixer/separator.

8. The system of claim 6 further comprising one or more processing units downstream of the BPA crystallizer stage, and wherein the one or more processing units produce recycle streams, and where one or more of the recycle streams are conveyed to the mixer/separator.

9. The system of claim 6 further comprising a solvent recovery unit, the solvent recovery unit recovering solvent used in the system and being coupled to at least one, or more of, the partial phenol removal unit or the mixer/separator to selectively adjust the composition of the product stream.

10. The system of claim 6 wherein the partial phenol removal unit is configured to adjust the composition of phenol in the product stream such that the product stream when fed to the BPA crystallizer stage does not contain more than 40 wt. % phenol.

11. A system for producing Bisphenol-A, comprising:
    a reactor unit wherein a product stream is produced including at least Bisphenol-A and Phenol;
    a partial phenol removal unit;
    a mixer/separator unit, the mixer/separator unit receiving the product stream from the reactor unit or the partial phenol removal unit and being configured to selectively adjust the composition of the product stream by mixing with one or more recycle streams;
    a solvent recovery unit, the solvent recovery unit recovering solvent used in the system and being coupled to at least one, or more of, the partial phenol removal unit or the mixer/separator to selectively adjust the composition of the product stream; and
    a BPA crystallizer stage, the crystallizer stage receiving the product stream and whereupon crystallization substantially pure Bisphenol-A crystals are produced directly upon crystallization in the BPA crystallizer stage, without prior adduct crystallization.

* * * * *